(12) United States Patent
Schornagel et al.

(10) Patent No.: US 11,607,232 B2
(45) Date of Patent: Mar. 21, 2023

(54) SYSTEM AND A DRILL BIT FOR DRILLING A BORE IN A BONE AND MEASURING A DEPTH OF THE BORE DURING SURGERY

(71) Applicant: SLAM Ortho B.V., Delft (NL)

(72) Inventors: Justus Baltus Laurensz Schornagel, The Hague (NL); Bart Kölling, Delft (NL); Bas De Hartog, Seacliff (AU)

(73) Assignee: SLAM Ortho B.V., Delft (NL)

( * ) Notice: Subject to any disclaimer, the term of this patent is extended or adjusted under 35 U.S.C. 154(b) by 165 days.

(21) Appl. No.: 16/954,018

(22) PCT Filed: Jan. 3, 2019

(86) PCT No.: PCT/EP2019/050102
§ 371 (c)(1),
(2) Date: Jun. 15, 2020

(87) PCT Pub. No.: WO2019/134942
PCT Pub. Date: Jul. 11, 2019

(65) Prior Publication Data
US 2021/0085340 A1  Mar. 25, 2021

(30) Foreign Application Priority Data

Jan. 8, 2018 (NL) .................................... 2020243

(51) Int. Cl.
*A61B 17/16* (2006.01)
*A61B 90/00* (2016.01)
*A61B 17/00* (2006.01)

(52) U.S. Cl.
CPC ...... *A61B 17/1617* (2013.01); *A61B 17/1622* (2013.01); *A61B 17/1626* (2013.01);
(Continued)

(58) Field of Classification Search
CPC . A61B 17/1617; A61B 90/06; A61B 17/1622; A61B 17/1626; A61B 2090/062;
(Continued)

(56) References Cited

U.S. PATENT DOCUMENTS 6,665,948 B1 * 12/2003 Kozin .................... A61B 90/06
175/45
2011/0196384 A1 * 8/2011 Pansky .............. A61M 25/0116
606/128
(Continued)

FOREIGN PATENT DOCUMENTS

DE       202004004699 U1    6/2004
NL          2020243 B1       7/2019
(Continued)

OTHER PUBLICATIONS

International Search Report & Written Opinion for PCT Application No. PCT/EP2019/050102 dated Jun. 5, 2019, 15 pages.

*Primary Examiner* — Kevin T Truong
*Assistant Examiner* — Diana Jones
(74) *Attorney, Agent, or Firm* — Bret E. Field; Bozicevic, Field & Francis LLP

(57) ABSTRACT

A system for drilling a bore in a bone (7) and measuring a depth of the bore during surgery, said system comprising: a drill (5) comprising a drill chuck (6) for holding a drill bit; a drill bit (3) mounted in the drill chuck; at least one sensor (11,12) arranged to produce signals for determining the depth of the bore, preferably comprising a strain gauge (11) arranged to produce a signal representing a force exerted on the system during drilling, and a distance sensor (12) arranged to produce a signal representing a distance between a reference point on the system and the bone surface during drilling; first communication means (19) arranged to communicate said signals to electronic processing means; electronic processing means (16) arranged to receive said signals
(Continued)

from said first communication means and to determine a depth of a bore from said signals; second communication means (13a) arranged to communicate said determined depth to output means; output means (2) for outputting information about the determined depth of the bore received from said second communication means; wherein said drill bit is part of a rotatable drill bit unit (1), which may or may not comprise said drill chuck; and said at least one sensor and one of said first and second communication means are mounted in the drill bit unit.

29 Claims, 5 Drawing Sheets

(52) U.S. Cl.
CPC .... *A61B 90/06* (2016.02); *A61B 2017/00221* (2013.01); *A61B 2090/062* (2016.02); *A61B 2090/066* (2016.02); *A61B 2562/0257* (2013.01); *A61B 2562/0261* (2013.01)

(58) Field of Classification Search
CPC .... A61B 2090/066; A61B 2017/00221; A61B 2562/0257; A61B 2562/0261
See application file for complete search history.

(56) References Cited

U.S. PATENT DOCUMENTS

| | | | |
|---|---|---|---|
| 2012/0035468 A1 | 2/2012 | Ritchey et al. | |
| 2013/0338669 A1* | 12/2013 | Brianza | A61B 17/88 606/80 |
| 2015/0066030 A1* | 3/2015 | McGinley | A61B 90/30 606/79 |
| 2016/0151120 A1* | 6/2016 | Kostrzewski | A61B 90/50 606/130 |
| 2016/0313868 A1* | 10/2016 | Weng | G06F 3/04883 |
| 2016/0361070 A1* | 12/2016 | Ardel | A61B 17/1617 |
| 2017/0181753 A1* | 6/2017 | Langeland | A61B 90/30 |
| 2017/0296204 A1* | 10/2017 | Matsuura | A61B 17/00 |
| 2017/0340282 A1 | 11/2017 | Ferro et al. | |
| 2019/0029697 A1* | 1/2019 | Anderson | A61B 17/1626 |
| 2021/0085340 A1 | 3/2021 | Schornagel et al. | |

FOREIGN PATENT DOCUMENTS

| | | |
|---|---|---|
| WO | WO2015034562 A1 | 3/2015 |
| WO | WO2017040783 A1 | 3/2017 |
| WO | WO2019134942 A1 | 7/2019 |

* cited by examiner

SYSTEM AND A DRILL BIT FOR DRILLING A BORE IN A BONE AND MEASURING A DEPTH OF THE BORE DURING SURGERY

The invention relates to a system for drilling a bore in a bone and measuring a depth of the bore during surgery, for instance orthopedic surgery, trauma surgery, neurosurgery, dental surgery, said system comprising: a drill comprising a drill chuck for holding a drill bit; a drill bit mounted in the drill chuck; at least one sensor arranged to produce signals for determining the depth of the bore; first communication means arranged to communicate said signals to electronic processing means; electronic processing means arranged to receive said signals from said first communication means and to determine a depth of a bore from said signals; second communication means arranged to communicate said determined depth to output means; output means for outputting information about the determined depth of the bore received from said second communication means. Said at least one sensor preferably comprising a strain gauge arranged to produce a signal representing a force exerted on the system during drilling and a distance sensor arranged to produce a signal representing a distance between a reference point on the system and the bone surface during drilling. Such a system is described in WO 2015/034562 A1. In this context, a signal representing a distance between a reference point on the system and the bone surface may mean a signal representing a distance between the reference point and the actual bone surface or between the reference point and for instance an orthopedic plate which is connected to the bone, or a drill sleeve which is placed against the bone surface.

There exists a desire to speed up and improve the drilling and measuring procedure during surgery. In most hospitals today the surgeon drills a hole through a bone and uses a separate tool afterwards to measure the diameter of the bone at that point. This information is then used to select the appropriate length screw for that hole. Systems as disclosed in WO 2015/034562 A1 automate this procedure by displaying the diameter of the bone directly to the surgeon after he has drilled the hole. The depth of the bore is determined by combining data about forces from the strain gauge and data about displacements from the distance sensor. The invention aims at an improved system.

To that end said drill bit is part of a rotatable drill bit unit, which may or may not comprise said drill chuck; and said at least one sensor and one of said first and second communication means are mounted in the drill bit unit. In the preferred embodiment said strain gauge is mounted on the drill bit unit arranged to produce a signal representing a force exerted on the drill bit unit during drilling and/or said distance sensor is a contactless distance sensor mounted in the drill bit unit arranged to produce a signal representing a distance between a reference point on the drill bit unit and the bone surface during drilling. In the preferred embodiment the drill bit unit comprises both said strain gauge mounted on the drill bit unit and said distance sensor mounted in the drill bit unit. Also in the system according to the invention the depth of a bore is determined in the well known manner of combining data about forces from the strain gauge and data about displacements from the distance sensor.

Preferably multiple strain gauges are mounted on the drill bit unit and arranged to produce signals representing both axial force and torque exerted on the drill bit unit. The strain gauge is preferably attached to the surface of the drill bit unit by an adhesive, such as cyanoacrylate. The strain gauge signals are preferably measured by using a Wheatstone bridge.

Preferably at least two distance sensors are mounted in the drill bit unit bit each arranged to produce a signal representing a distance between a reference point on the drill bit unit and the bone surface during drilling, said distance sensors and said reference points extending at radially opposite sides of the drill bit. Said distance sensor or sensors are preferably electromagnetic time-of-flight sensors, more preferably infrared time-of-flight sensors.

Preferably also said first communication means are mounted in the drill bit unit, said processor means are mounted in the drill bit unit, and said second communication means mounted in the drill bit unit. Preferably also a power source such as a battery for powering the strain gauge, the distance sensor and/or the communication means is mounted in the drill bit unit.

Although communication means with slip contacts between the rotating drill bit unit and the drill may be used, preferably said first or second communication means are wireless communication means.

The drill bit unit preferably comprises a housing extending around the drill bit and encapsulating each of said strain gauge(s), distance sensor(s), communication means, power source, processing means and other electronic components, as far as they are mounted in the drill bit unit.

The drill bit unit is preferably releasably mounted in the drill chuck. Preferably said strain gauge is mounted on the drill bit. As an alternative, said strain gauge is mounted on the drive shaft of the drill chuck.

The output means preferably comprise a display for displaying information about the determined depth of the bore received from said second communication means.

The invention also relates to a drill bit unit for mounting in a drill for drilling a bore in a bone and measuring a depth of the bore during surgery, said drill bit unit comprising: a drill bit; at least one sensor arranged to produce signals for determining the depth of the bore; and communication means arranged to communicate said signals or a determined value derived therefrom to an external device.

The invention will be exemplified by means of an embodiment and with reference to the drawings, wherein.

Figure 1:
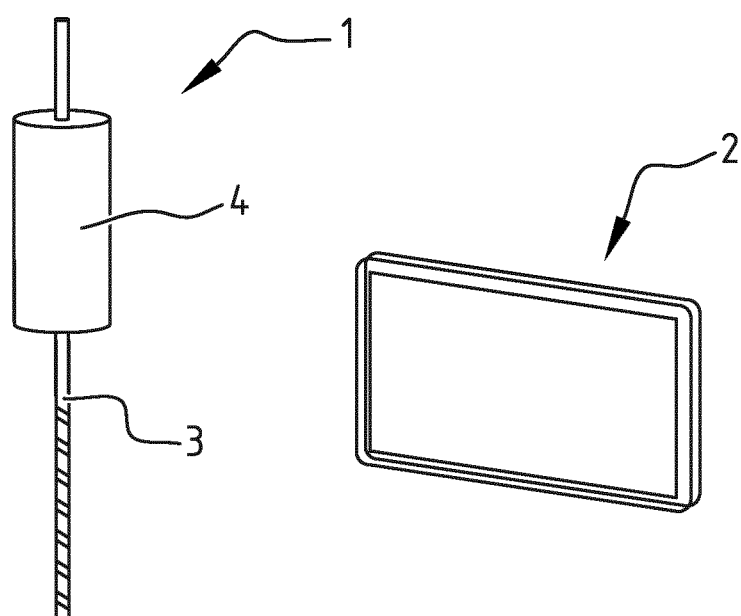
FIG. 1 is a schematic perspective view of a drill bit unit and output means of a system in accordance with the invention.
Figure 2:
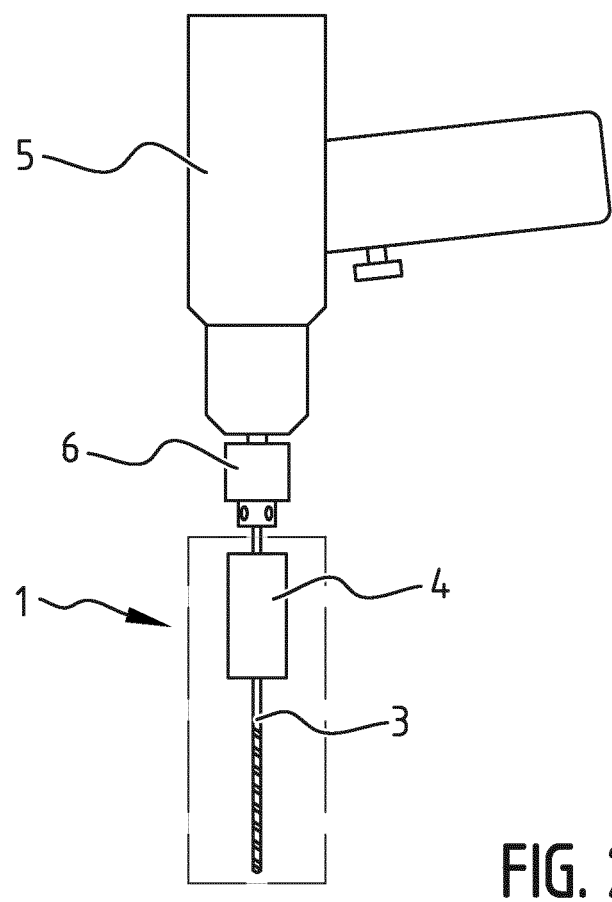
FIG. 2 is a schematic side view of a system in accordance with the invention.
Figure 3:
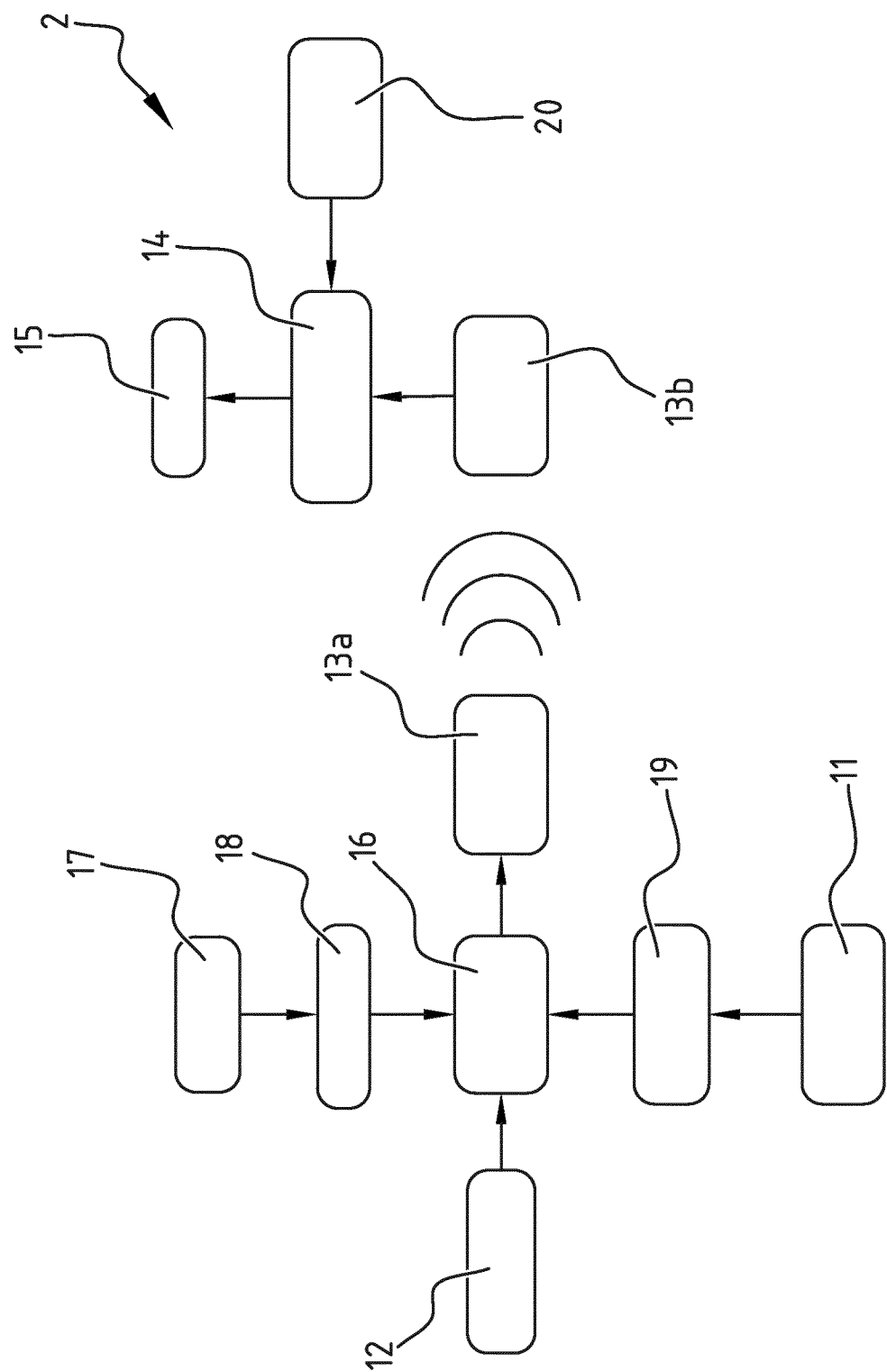
FIG. 3 is a schematic functional overview of a system in accordance with the invention.

According to FIG. 1 the system according to the invention comprises a drill bit unit, comprising a drill bit 3 and a component housing 4. The system further comprises a data processing and display unit 2. According to FIG. 2 the drill bit unit 1 is releasably mounted in the drill chuck 6 of a drill 5. The drill chuck 6 comprises a driven shaft which is connected to the motor of the drill.

Figure 4:
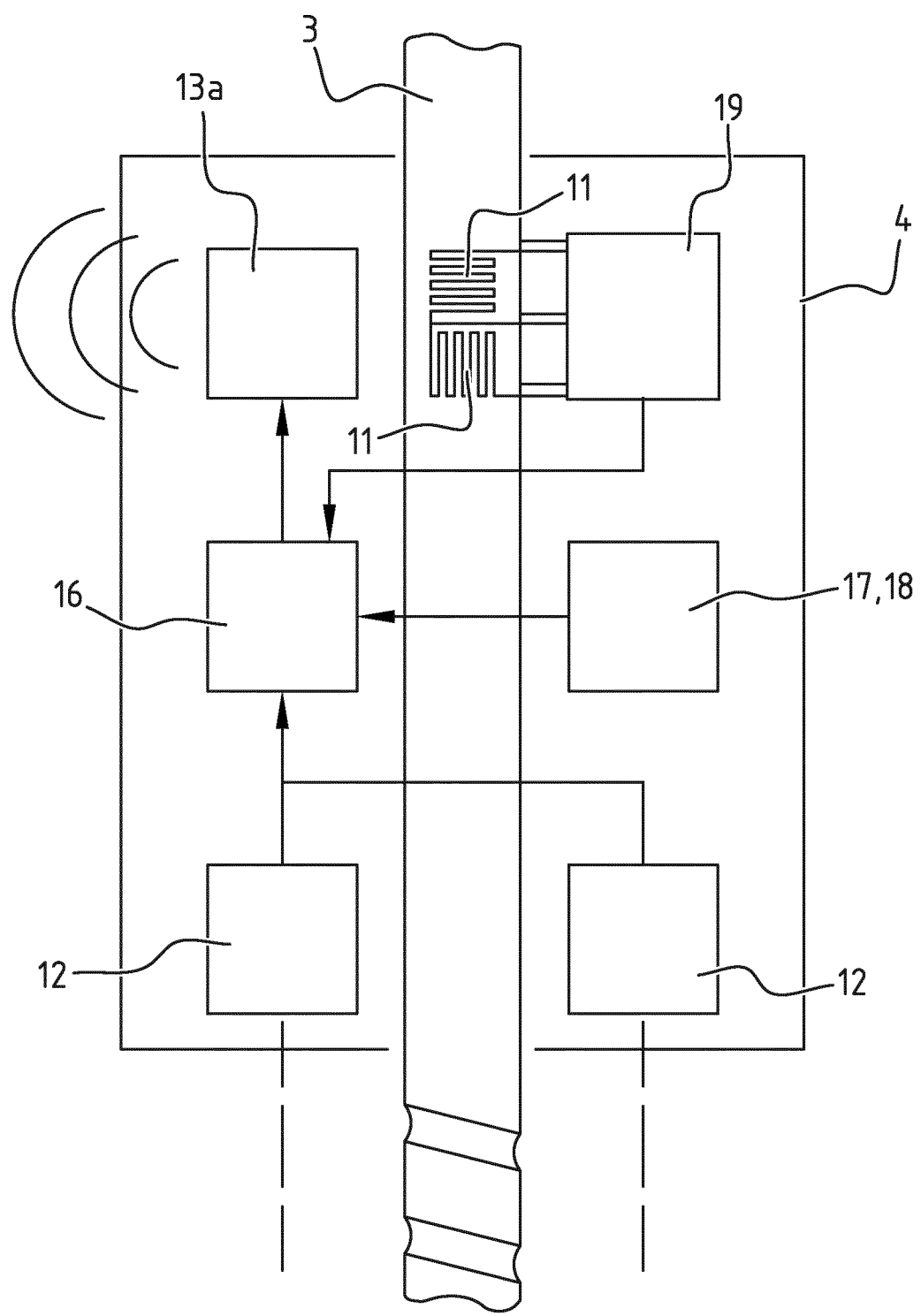
FIG. 4 is a schematic structural overview of a system in accordance with the invention.
Figure 5:
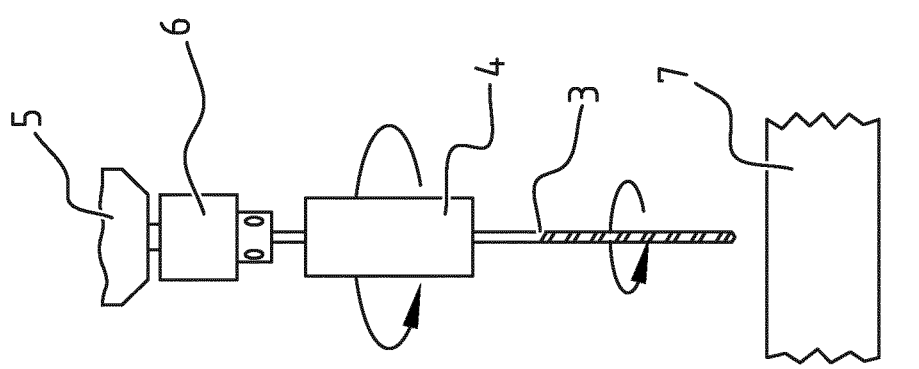

According to FIGS. 4 and 5 the component housing 4 comprises a microcontroller 16 which is connected to the following components:

- strain gauges 11 which are attached to the drill bit 3 by a strong adhesive, and connected to the microcontroller via voltage amplifiers 19, such as an analog-to-digital converter;
- two distance sensors 12, such as infrared time-of-flight laser sensors, which are mounted on opposite sides of the drill bit facing downward;
- a wireless transmitter 13a, such as a RF 2.4 GHz transceiver; and
- a battery 17, such as a small 3.7 Volt lithium-ion cell via a voltage regulator 18 to 3.3 Volt.

As an alternative, the strain gauges 11 may be attached to the drive shaft of the drill chuck 6, and also the other components may be housed inside or on the drill chuck 6.

The data processing and display unit 2 may for instance comprises a mobile device, a tablet device or a personal computer 14, which is connected to or comprises a wireless receiver 13b, such as a RF 2.4 GHz transceiver, a display 15 and a user input device 20.

Figure 7:
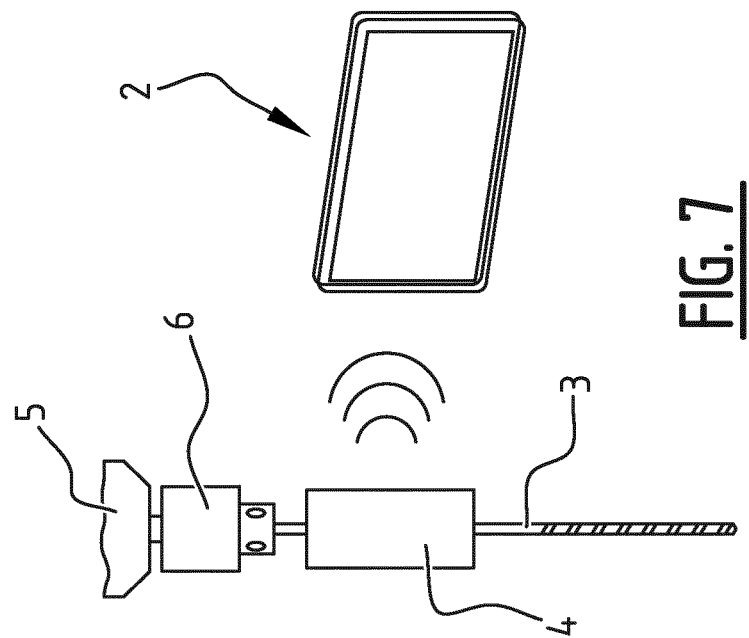
FIGS. 5, 6 and 7 are front views of a system in accordance with the invention in three different stages of drilling and measuring.
Figure 6:
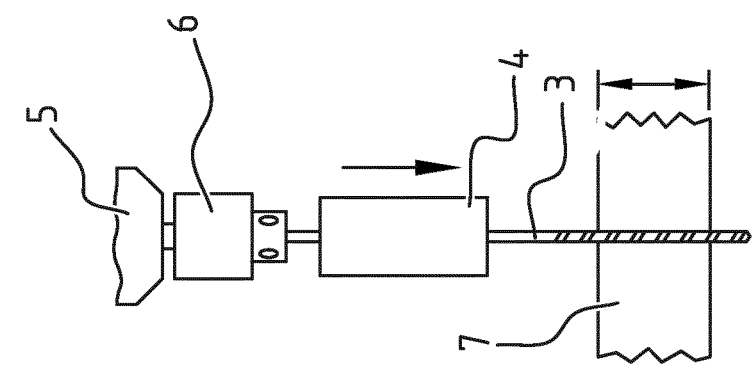

According to FIGS. 5, 6 and 7, the steps during drilling of one hole are shown, wherein in FIG. 5 the drilling is started, and the measurement system inside the casing 4 rotates with the drill bit 3 and measures the displacement and the force on the drill. In FIG. 6 the drilling is complete, and in FIG. 7 the data is sent to the processing and display unit 2 which displays the depth of the object that was measured.

Figure 8:
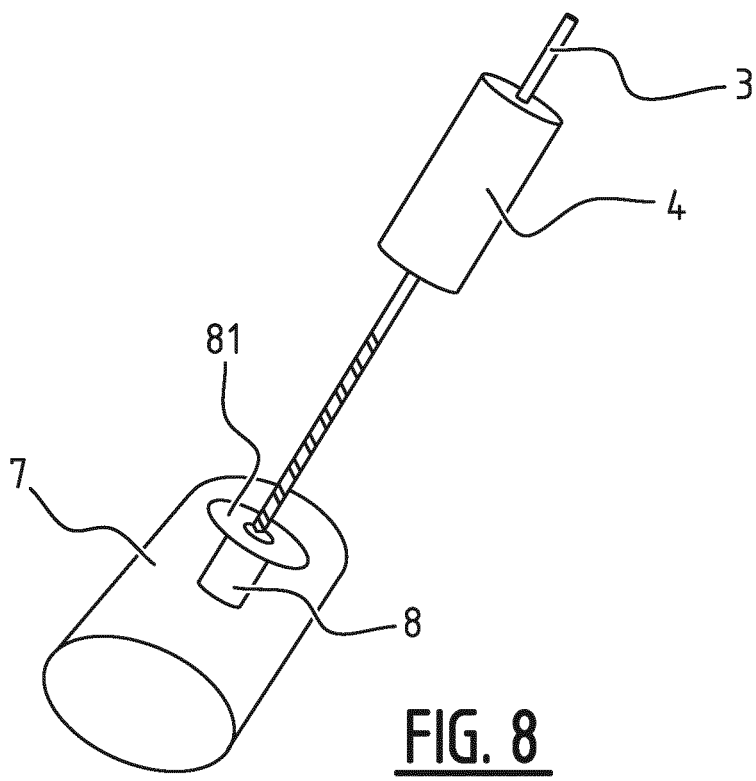
FIG. 8 is a schematic perspective view of a drill bit unit used in combination with a drill sleeve in accordance with the invention.

According to FIG. 8 the system may be used in combination with a drill sleeve 8 for guiding the drill during operation, wherein the drill sleeve has a reflective surface 81 for reflecting the electromagnetic signals of the distance sensors 12.

Figures 9, 10:
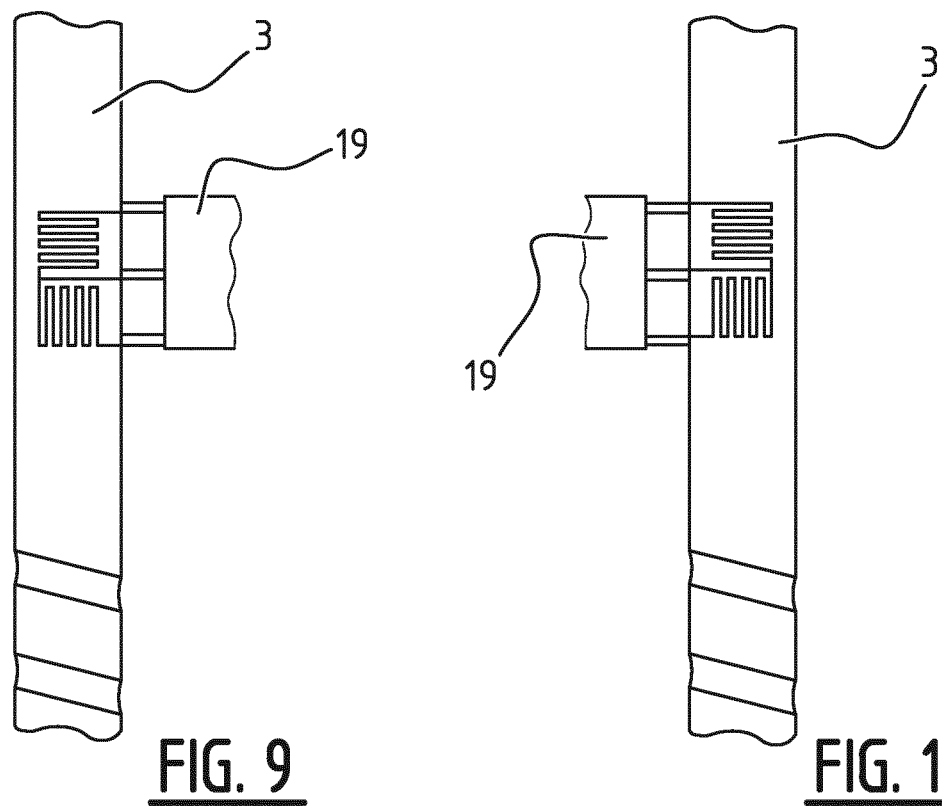
FIGS. 9 and 10 are respective schematic front and back views of a detail of the drill bit unit in accordance with the invention.

According to FIGS. 9 and 10 the strain gauges 11 are mounted on two opposite sides of the drill bit 3, in two pairs of gauges 11, in such a way that they are sensitive to axial forces and cancel out force bending in the drill bit 3.

The system thus consists of a measuring part 4, 11, 12, 13a, 16, 17, 18, 19 rotating with the drill bit 3 and a displaying part 2 separate from it showing the result of the measurement. The measurement system consists of sensors 11, 12 and electronics 13a, 16, 17, 18, 19 in an encasing 4 that is mounted to an orthopedic drill bit 3 permanently. This system measures the distance to a surface that is being drilled into and measures the axial force during this drilling procedure. The data that is collected is then sent to the display system 2 wirelessly.

Apart from this the system contains other electronic components, such as wires, resistors, capacitors (not shown), and uses some form of encapsulation to protect the components. The transmitter 13a transmits the data during the drilling procedure. The measurement system works when drilling through one solid object or a hollow object. When drilling in a bone 7 the system will often encounter such a hollow structure.

The system uses the strain gauges 11 in a Wheatstone bridge configuration to allow maximum sensitivity to axial force, thus in the direction of the drilling motion. This configuration needs a voltage amplifier 19 to amplify the signal from this bridge. This amplified signal is then fed to the microcontroller 16.

The distance sensors 12 are contactless sensors which measure a distance through the air with electromagnetic waves. The system uses multiple distance sensors 12 to measure the distance to the surface of the object 7 the drill is entering. Multiple sensor measurements can be used to reduce the noise in the measured distance. The measurements are sent to the microcontroller 16.

The displaying part 2 is a sub-system separated from the drill 5 and can be implemented in various ways. It can be done with a personal computer, a mobile device or a dedicated device with a display.

The displaying part receives measurements wirelessly from the measurement system and processes the data. The force and distance data is combined to calculate a point where the bone 7 starts and where it ends. This results in the recommended screw length which is displayed to the surgeon.

The displaying part can be used with multiple variations of the measurement system and the user can set with what type of orthopedic plates and screws the system works. The displaying part can also store data from multiple drilling procedures.

In summary, the automatic measuring drilling system has sensors 11, 12 and electronics 13a, 16, 17, 18, 19 mounted on a drill bit. The sensors 11, 12 measure axial force with strain gauges 11 and measure the distance to the surface that is being drilled into without contact through sensors 12. The data is used by the display part to calculate the diameter of the bone 7 it drilled into and recommends a screw length to the use.

Advantages of the disclosed system are, amongst others:
- it can be used on existing drill systems that will not have to be replaced;
- it ensures proper sensor alignment to the to be measured surface as the distance sensors will always be parallel with the movement trajectory of the drilling system;
- it is ergonomic, as the distance sensor is placed such that it will not interfere with the surgeon holding the drill;
- the strain gauges are placed in such a way that the signal is strongest and most clear, as the diameter of the material of the drill bit or the drill chuck is relatively small and the strain will therefore be relatively large; and
- using the drill bit as the information carrier/processor has the following advantages:
  - the algorithm is set for a specific diameter drill bit and forces without a need to select or identify the diameter or type of drill bit;
  - drill bits can be used solely with a specific instrument set, as opposed to drill machines that are shared between all instrument sets, and hence specific instrument set properties such as orthopedic plate thickness, drill sleeve length, drill bit length itself can be preprogrammed, reducing the need for additional identification steps or selection of specific instrument set components.

The invention has thus been described by means of preferred embodiments. It is to be understood, however, that this disclosure is merely illustrative. Various details of the structure and function were presented, but changes made therein, to the full extent extended by the general meaning of the terms in which the appended claims are expressed, are understood to be within the principle of the present invention. The description and drawings shall be used to interpret the claims. The claims should not be interpreted as meaning that the extent of the protection sought is to be understood as that defined by the strict, literal meaning of the wording used in the claims, the description and drawings being employed only for the purpose of resolving an ambiguity found in the claims. For the purpose of determining the extent of protection sought by the claims, due account shall be taken of any element which is equivalent to an element specified therein. An element is to be considered equivalent to an element specified in the claims at least if said element performs substantially the same function in substantially the same way to yield substantially the same result as the element specified in the claims.

The invention claimed is:

1. A system for drilling a bore in a bone and measuring a depth of the bore during surgery, said system comprising:
   a drill comprising a drill chuck for holding a drill bit;
   a drill bit mounted in the drill chuck;
   at least one sensor arranged to produce signals for determining the depth of the bore;
   first communication means arranged to communicate said signals to electronic processing means;
   electronic processing means arranged to receive said signals from said first communication means and to determine a depth of a bore from said signals;
   second communication means arranged to communicate said determined depth to output means;
   output means for outputting information about the determined depth of the bore received from said second communication means;
   characterized in that
   said drill bit is part of a rotatable drill bit unit, which may or may not comprise said drill chuck; and
   said at least one sensor and one of said first and second communication means are mounted in the drill bit unit.

2. The system of claim 1, wherein said at least one sensor, arranged to produce said signals for determining the depth of the bore, comprises:
   a strain gauge arranged to produce a signal representing a force exerted on the system during drilling for determining the depth of the bore; and
   said strain gauge is mounted on the drill bit unit arranged to produce a signal representing a force exerted on the drill bit unit during drilling for determining the depth of the bore.

3. The system of claim 2, wherein said at least one sensor, arranged to produce said signals for determining the depth of the bore, further comprises:
   a distance sensor arranged to produce a signal representing a distance between a reference point on the system and a bone surface during drilling for determining the depth of the bore; and
   said distance sensor is a contactless distance sensor mounted in the drill bit unit arranged to produce the signal representing the distance between the reference point on the drill bit unit and the bone surface during drilling for determining the depth of the bore.

4. The system of claim 3, wherein both the strain gauge is mounted on the drill bit unit and the distance sensor is mounted in the drill bit unit.

5. The system of claim 2, wherein multiple strain gauges are mounted on the drill bit unit and arranged to produce signals representing both axial force and torque exerted on the drill bit unit.

6. The system of claim 2, wherein the strain gauge is attached to the surface of the drill bit unit by an adhesive, such as cyanoacrylate.

7. The system of claim 2, wherein the strain gauge signals are measured by using a Wheatstone bridge.

8. The system of claim 2, wherein at least two distance sensors are mounted in the drill bit unit each arranged to produce a signal representing a distance between a reference point on the drill bit unit and the bone surface during drilling, said distance sensors and said reference points extending at radially opposite sides of the drill bit.

9. The system of claim 2, wherein said distance sensor or sensors are electromagnetic time-of-flight sensors, preferably infrared time-of-flight sensors.

10. The system of claim 2, wherein said strain gauge is mounted on the drill bit.

11. The system of claim 2, wherein the drill chuck comprises a drive shaft, and said strain gauge is mounted on said shaft.

12. The system of claim 1, wherein said first communication means are mounted in the drill bit unit, said processor means are mounted in the drill bit unit, and said second communication means are mounted in the drill bit unit.

13. The system of claim 1, wherein a power source such as a battery for powering the sensor(s) and/or the communication means is mounted in the drill bit unit.

14. The system of claim 1, wherein said first or second communication means are wireless communication means.

15. The system of claim 1, wherein the drill bit unit comprises a housing extending around the drill bit and encapsulating each of said sensor(s), communication means, power source, processing means and other electronic components, as far as they are mounted in the drill bit unit.

16. The system of claim 1, wherein said output means comprise a display for displaying information about the determined depth of the bore received from said second communication means.

17. The system of claim 1, wherein the drill bit unit is releasably mounted in the drill chuck.

18. The system of claim 1, wherein said at least one sensor, arranged to produce said signals for determining the depth of the bore, comprises:
   a distance sensor arranged to produce a signal representing a distance between a reference point on the system and a bone surface during drilling for determining the depth of the bore; and
   said distance sensor is a contactless distance sensor mounted in the drill bit unit arranged to produce the signal representing the distance between the reference point on the drill bit unit and the bone surface during drilling for determining the depth of the bore.

19. A drill bit unit for drilling a bore in a bone and measuring a depth of the bore during surgery, said drill bit unit comprising:
   a drill bit;
   at least one sensor arranged to produce signals for determining the depth of the bore;
   communication means arranged to communicate said signals or a determined value derived therefrom to an external device,
   characterized in that
   said drill bit unit is a rotatable drill bit unit.

20. The drill bit unit of claim 19, wherein said at least one sensor, arranged to produce said signals for determining the depth of the bore, comprises a strain gauge mounted on the drill bit unit arranged to produce a signal representing a force exerted on the drill bit unit during drilling for determining the depth of the bore, and/or a contactless distance sensor mounted in the drill bit unit arranged to produce a signal representing a distance between a reference point on the drill bit unit and the bone surface during drilling for determining the depth of the bore.

21. The drill bit unit of claim 20, wherein the drill bit unit comprises both said strain gauge mounted on the drill bit unit and said depth sensor mounted in the drill bit unit.

22. The drill bit unit of claim 20, wherein multiple strain gauges are mounted on the drill bit unit and arranged to produce signals representing both axial force and torque exerted on the drill bit unit.

23. The drill bit unit of claim 20, wherein the strain gauge is attached to the surface of the drill bit unit by an adhesive, such as cyanoacrylate.

24. The drill bit unit of claim 20, wherein the strain gauge signals are measured by using a Wheatstone bridge.

25. The drill bit unit of claim 20, wherein at least two distance sensors are mounted in the drill bit unit each arranged to produce a signal representing a distance between a reference point on the drill bit unit and the bone surface during drilling, said distance sensors and said reference points extending at radially opposite sides of the drill bit.

26. The drill bit unit of claim 20, wherein said distance sensor or sensors are electromagnetic time-of-flight sensors, preferably infrared time-of-flight sensors.

27. The drill bit unit of claim 19, wherein a power source such as a battery for powering the sensor and/or the communication means is mounted on the drill bit unit.

28. The drill bit unit of claim 19, wherein said communication means are wireless communication means.

29. The drill bit unit of claim 19, wherein the drill bit unit comprises a housing extending around the drill bit unit and encapsulating each of said sensor(s), communication means, power source, processing means and other electronic components, as far as they are mounted in the drill bit unit.

* * * * *